United States Patent [19]

Alexander et al.

[11] Patent Number: 4,970,206

[45] Date of Patent: Nov. 13, 1990

[54] PYROGLUTAMIC ACID ESTERS USED AS DERMAL PENETRATION ENHANCERS FOR DRUGS

[75] Inventors: Jose Alexander; Takeru Higuchi, both of Lawrence, Kans.

[73] Assignee: Merck & Co., Inc., Rahway, N.J.

[21] Appl. No.: 348,914

[22] Filed: May 8, 1989

Related U.S. Application Data

[60] Division of Ser. No. 220,853, Jul. 18, 1988, Pat. No. 4,847,250, which is a continuation-in-part of Ser. No. 802,907, Nov. 29, 1985, Pat. No. 4,762,851.

[51] Int. Cl.$^5$ ................ A61K 31/56; A61K 31/58
[52] U.S. Cl. .................... 514/174; 514/179; 514/180
[58] Field of Search .................. 514/174, 179, 180

*Primary Examiner*—Stanley J. Friedman
*Attorney, Agent, or Firm*—Joseph F. DiPrima; Manfred Polk

[57] ABSTRACT

The invention relates to pyroglutamic acid esters used as dermal penetration enhancers for therapeutic agents having poor skin permeation.

20 Claims, No Drawings

PYROGLUTAMIC ACID ESTERS USED AS DERMAL PENETRATION ENHANCERS FOR DRUGS

CROSS REFERENCE TO RELATED APPLICATIONS

This is a division application of U.S. Ser. No. 220,853 filed July 18, 1988, now U.S. Pat. No. 4,847,250, which in turn, is a continuation-in-part of U.S. application Ser. No. 802,907 filed Nov. 29, 1985, now U.S. Pat. No. 4,762,851.

BACKGROUND OF THE INVENTION

The invention relates to novel compositions and methods for enhancing permeation of topically administered drugs by incorporating therein pyroglutamic acid esters as dermal penetration enhancing agents.

Transdermal drug delivery to achieve systemic effect is an area of much current interest and activity. While the cutaneous route of input is advantageous in many respects such as ease of use, better patient compliance, decreased first pass metabolism etc., the excellent barrier nature of the skin has so far limited the drugs considered suitable for transdermal delivery to very few. The use of adjunctive chemicals known as skin penetration enhancers widens the scope of transdermal drug delivery. Such use involves controlled impairment of the skin's protective layer, the stratum corneum. Ideally, no elements of the skin other than this horny layer should be involved in such a drug delivery approach, because participation of any living tissue could result in cellular insult and lead to an irritant or allergic response. So an ideal penetration enhancer is one which speeds the permeation of the drug through the stratum corneum, without itself crossing this barrier, or if it crosses, undergoes fast metabolic destruction and/or detoxification in the viable area of the skin. This invention deals with an analagous series of penetration enhancers of the latter type.

It is well known that a number of therapeutically active agents, such as β-blockers, antihypertensives, antiarrhythmics, antiangingl agents, vasodilators, antiemetics, antibacterials, antifungals, corticosteroids, antiinflammatories and the like when administered to warm-blooded animals by a number of various routes such as by intravenous infusion, intramuscular injection, oral, rectal or buccal routes, enter the general circulation and produce the appropriate systemic therapeutic effect. It is also known that the aforementioned methods of administration have certain disadvantages. For example, the intravenous and intramuscular routes are not only painful for the patient, but also must be performed by a trained individual. Buccal and rectal administration often produce discomfort and annoyances for the patient. Oral administration, although generally acceptable for the patient, often does not deliver much of the therapeutic agent to systemic circulation. This diminished drug delivery is usually attributed to poor absorption from the gastrointestinal tract and/or to degradation of the agent by the acidic medium of the stomach, by the enzymes in the gastrointestinal tract and surrounding tissue, or by the rapid metabolism by enzymes of the liver through which the drug must pass before it enters the systemic circulation. For example, drugs such as anti bacterials, narcotic analgesics, β-blockers and others require relatively high doses when given orally due to the remarkable liver metabolism encountered.

Effective delivery of such drugs through the skin would require much lower doses because the so called "first pass" metabolism would be avoided. Additionally, the topical application of the drug has the advantage that their pharmacological action is exhibited gradually over an extended period of time avoiding the possibility of inducing undesirable physiological action by abrupt increase in concentration in vivo.

But most drugs are not absorbed in sufficient concentration through the skin to exhibit pharmacological effect. This is because skin is an effective barrier to penetration. The outer layer of the epidermis, called the stratum corneum, offers the maximum resistance to penetration, whereas the lower-layers are relatively permeable. For proper treatment of dermal conditions, it is important that the active agent penetrate the stratum corneum where it is retained. From this reservoir in the outer layer, the therapeutic agent could be slowly released and penetrates the underlying areas where it could exhibit its therapeutic or cosmetic effect. When dermatological agents such as sunscreens, which protect the underlying tissue from external factors (ultraviolet rays) are used, maximum retention in the stratum corneum is essential. On the other hand, the relative permeability of the layers of the epidermis below the stratum corneum can also allow access to the systemic circulation; indeed, it is necessary for the therapeutic agent to penetrate the stratum corneum in order to provide systemic therapeutic effect from the transdermal route.

DESCRIPTION OF THE PRIOR ART

Many investigators have turned to various enhancing agents such as dimethylsulfoxide, dimethylformamide and various other aliphatic and aromatic amides, cyclic amides (Akerman et al., Pharmacol. et Toxicol. 1979, 45, 58), methyldecylsulfoxide (U.S. Pat. No. 527,864), dimethyl acetamide (U.S. Pat. No. 3,472,931) and the like to deliver topically active agents more efficiently through the skin, as well as to enhance the absorption of systemically active therapeutic agents through the skin into general circulation. U.S. Pat. No. 3,989,816 discloses that 1-substituted azacyclopetane-2-one derivatives enhance penetration of a physiologically active agent through the skin. U.S. Pat. No. 3,920,814 discloses that the antibacterial activity of antibiotics such as penicillins and cephelosporins is potentiated by coadmininstration with pyrrolidone carboxylic acid or a salt derivative thereof. The reference directs itself to oral and intravenous forms of administration. U.S. Pat. No. 3,836,665 discloses a topical dermatological composition for cosmetic sebacious gland excretion-inhibiting treatment or therapeutic antiphlogistic treatment of the skin consisting of an inert dermatological carrier and alkyl esters of 5-pyrolidone-2-carboxylic acid. Finally, European Patent Application No. 0123948A1 (1984) claims glycerol pyroglutamates wherein one or both of the glycerol hydroxyls etherified with alkyl or alkenyl groups as shown below a penetration enhancers:

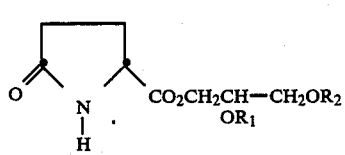

The similarity of the side chain in the above mentioned application to nonionic surfactants and the use of such agents in enhancing the penetration of medication through mucous membranes of warm blooded animals has been studied heretofore. In fact, Japanese Patent Application No. 2961/1984 teaches that pyroglutamic acid monoglycerides have surface active action and are effective emulsifiers, penetrants, detergents, spreaders and antistatic agents and are considered to have skin protecting acion. However, our discovery that simple alkyl and alkenyl esters of pyroglutamic acid which do not have the non-ionic-surfactant-like side chain are skin penetration enhancers is unanticipated and unobvious. In fact, our compounds have certain advantages over the others: (1) the alkyl and alkenyl esters do not show skin irritation on occlusive application for 24 hours, whereas the glyceride esters show erythema on application for 24 hours; (2) the alcohols derived from hydrolysis of our compounds are non-toxic and are endogenous substances or metabolic precursors of fatty acids whereas some glycerol ethers are known to be potent mutagens (J. Am. Chem. Soc 1982, 104, 6149).

SUMMARY OF INVENTION

This invention relates to pyroglutamic acid ester used as dermal penetration enhancers for thereapeutic agents having poor skin permeation.

Accordingly, it is an object of the invention to provide a novel concept in skin penetration enhanced drug delivery, namely, the use of penetration enhancers that undergo metabolic destruction when they cross the stratum corneum into the viable area of the skin tissue.

A further obJect of the invention is to provide a novel class of skin penetration enhancers which after achieving their function of promoting the permeation of a drug or medicament through the stratum corneum, undergo fast metabolic breakdown into nontoxic metabolic products as soon as they reach the live area of the skin.

Another object of the present invention is to provide a novel class of penetration enhancers, which will enhance the dermal absorption of therapeutic or cosmetic agents, such enhancers being capable of improving delivery through the skin and into the general circulation of systemically active drugs.

Another object is to provide penetration enhancing agents devoid of toxic side effects by virtue of fast metabolic breakdown as they come into contact with living tissue.

Still another object of this invention is to provide a class of penetration enhancing agents whose breakdown products are endogenous, or precursors of endogenous substances which can be metabolized through normal pathways available in the body.

Yet another object of the invention is to provide novel compositions utilizing the aforementioned enhancing agents for topical application and novel methods of enhancing the skin penetration of therapeutic agents.

These and other objects and advantages of the invention will become apparent from the following description.

DESCRIPTION OF THE INVENTION

The invention is concerned with novel compositions and methods for enhancing the permeation of topically administered drugs by incorporating therein a pyroglutamic acid ester as a dermal penetration enhancing agent for said drugs. The dermal penetration enhancing agents are described according to the general structural formula below:

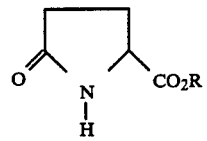

wherein R is a straight or branched chain alkyl ($C_5$–$C_{20}$) such as pentyl, heptyl, octyl, decyl, dodecyl, tetradecyl, hexadecyl, octadecyl, stearyl, eicosyl and the like; alkenyl ($C_5$–$C_{20}$) with 1-6 double bonds such as pentenyl, octenyl, decenyl, dodecenyl, farnesyl, oleyl and the like; hydroxylalkyl ($C_5$–$C_{20}$) with 1 to 3 hydroxy groups such as hydroxypentyl, hydroxydecyl, hydroxyhexadecyl, dihydroxyoctadecyl and the like; ketoalkyl ($C_5$–$C_{20}$) such as 2-ketapentyl, ketododecyl, ketohexadecyl and the like; unsaturated hydroxyalkyl ($C_5$–$C_{20}$) such as hydroxyoctenyl, hyroxydodecenyl, hydroxyhexadecenyl and the like; carboxyalkyl ($C_5$–$C_{20}$) such as $\omega$-carboxyoctyl, $\omega$-carboxyhexadecyl and the like or alkoxycarbonylalkyl ($C_5$–$C_{20}$) such as ethoxycarbonylhexyl, ethoxycaronyldodecyl and the like.

The pyroglutamic esters of the invention are known compounds and processes for their preparation are known in the art.

In accord with the foregoing objects, the invention provides a novel composition of matter for topical application comprising at least one drug or therapeutic agent and an ester of pyro-glutamic acid and further comprises, if desired, a non-toxic topical pharmaceutically acceptable carrier. The therapeutic agent is present in a biologically effective amount, i.e., in an amount sufficient to produce the desired biological effect. Thus, when the therapeutic agent is a dermatological agent, it is utilized in a dermally effective amount, i.e., in an amount sufficient to evoke the desired dermal effect (which may be cosmetic or therapeutic in nature). On the other hand, when the therapeutic agent is systemically active and introduction of the agent into the general circulation is desired then the amount is employed in a systemically effective amount, i.e., in an amount sufficient to produce the desired systemic response. Pyroglutamate ester is employed in such compositions in an amount sufficient to enhance skin permeation of the therapeutic agent.

Various active agents provide beneficial effects when administered to patients. Such agents which can be made more useful by enhancing its absorption in accordance with this invention, are exemplified by, but not limited to, the following classes of agents:

(A) Antiarrythmic: Bucainide, diisopyramide, encainide, tocainide, verapamil, and the like;
(B) Antihypertensive such as clonidine, enalapril, hydralazine, prazosin, α-methyldopa and the like;
(C) Antivirals such as acyclovir, cytarabine, enviroxime, floxuridine, ribavarin, vidarabine, idoxuridine, trifluriding and the like;
(D) β-Blockers such as propranolol, bupranolol. metoprolol, atenolol, pindolol, betaxalol, timolol, sotalol, alprenolol, nadolol, oxprenolol and the like;
(E) Diuretics such as aldactone, hydrochlorothiazide, ticrynafer and the like;

(F) Non-steroidal antiinflammatory agents, such as indomethacin, naproxen, fenoprofen, ibuprofen, alcolfenac, phenylbutazone, mefenamic acid, diflunisal, sulindac, desoxysulindac, aspirin, salicylamide, salicylic acid, oxyphenbutazone, apazone, cintazone, flufenamic acid, meclofenamic acid, flunixin, dimefadane, indoxole, intrazole, mimbane hydrochloride, paranylene hydrochloride, tetrydamine, benzindopyrine hydrochloride, fluprofen, ibufenac, ketoprofen, naproxol, fenburan, cinchophen, diflumidon sodium, fenamole, flutiazin, metazamide, letimide hydrochloride, nexeridine hydrochloride, octazamide, molinazole neocinchophen, nimazole, proxazole citrate, tesicam, tesimide, tolmetin, tramadol, triflumidate and the like;

(G) Steroidal antiinflammatory agents, i.e., corticosteroids, such as hydrocortisone, hydrocortisone 17-valerate, hydrocortisone 17-butyrate, hydrocortisone 21-acetate, betamethasone valerate, triamcinolone acetonide, fluocinonide, desonide, fluocinolone acetonide, dexamethasone, prednisolone, haloprednone, cortisone acetate, cortisone cyclopentylpropionate, cortodoxone, flucetonide, fludrocortisone acetate. flurandrenolone acetonide, medrysone, amcinafal, amcinafide, betamethasone, betamethasone benzoate, chloroprednisone acetate, clocortolone acetate, descinolone acetonide, desoximetasone, dichlorisone acetate, difluprednate, flucloronide, flumethasone, flunisolide acetate, fluocortolone, fluorometholone, fluperolone acetate, fluprednisolone, fluprednisolone valerate, meprednisone, methyl prednisolone, paramethasone acetate, prednisolamate, prednisone, prednival, triamcinolone, triamcinolone hexacetonide, cortivazol, formocortal, nivazol and the like;

(H) Muscle relaxants such as theophylline, cyclobenzaprine, aminophylline, diphylline, oxtriphylline, ambutylline, fenethylline, guathylline, pentoxyfylline, xanthinol niacinate, theophylline glycinate, glucopylline and the like;

(I) Polypeptides such as cyclo-(N-Me-Ala-Tyr-D-Trp-Lys-Val-Phe)actetate, somatostatin, insulin, gastrin, caerulein, cholecystokinin and the like;

(J) Coronary Vasodilators such as, diltiazem, dipyridamole, erythritol tetranitrate, nifedipine and the like;

(K) Prostanoids such as rioprostil, viprostil, doxaprost, enisoprost, enprostil and the like; and (L) Dual lipoxygenase-cycloxygenase inhibitors such as 2,3-dihydro-5-hydroxy-6-(o-hydroxymethylcinnamyl)benzofuran and the like.

The enhancement of drug absorption in accordance with this invention is not by any means limited to the above drugs, but are in general applicable to other classes of drugs such as analgesics, anabolics, androgens, anorexics, adrenermics, antiadrenergics, antiallergics, antibacterials, anticholinermics, antidepressants, antidiabetics, antifungal agents, antihypertensives, antineoplastics, antipsychotics, sedatives, cardiovascular agents, antiulcer agents, anticoagulants, anthelmintics and the like.

The amount of drug varies over a wide range but in general the therapeutically effective unit dosage amount of the selected drug depends on that amount known in the art to obtain the desired results.

Generally, the amount of enhancing agent employed in the practice of this invention ranges from 0.75 mg to 1 g in each unit dose. The weight percentage of enhancing agent in the total combination of drug plus agent is 5-99% with a preferred ratio of enhancing agent in the total combination of agent plus drug being 10-40%.

The following examples illustrate preparation of various compositions of the invention. The examples should be construed as illustrations rather than limitations thereof.

EXAMPLE 1

Decyl Pyroglutamate

To an ice cold suspension of pyroglutamic acid (1.3 g) and n-decanol (1.6 g) in dichloromethane (50 ml), dicyclohexylcarbodiimide (2.1 g) and 4-dimethylaminopyridine (0.1 g) were added. After stirring at ice bath temperature for 2 hours, the cooling bath was removed and the mixture was stirred at room temperature overnight. The michloromethane was evaporated off. The residue was taken in ether and filtered. The filtrate was washed with 1N HCl, water, aqueous bicarbonate and water. It was then dried over $Na_2SO_4$ and evaporated. The residue weighed 2.75 g. It was chromatographed over silica gel. The pure decyl ester was eluted with ethylacetate-chloroform (1:4), 2.3 g m.p. 34°-35°.

n-Dodecyl, farnesyl an oleyl pyroglutamates were prepared similarly and purified by chromatography.

EXAMPLE 2

Rat plasma hydrolysis of decyl pyroglutamate

Freshly prepared rat plasma (2 ml) was mixed with decyl pyroglutamate (0.6 mg) and was maintained at 37° C. Aliquots were removed at different time intervals and vortexed with heptane (1 ml) containing dodecanol as an internal standard. The decanol produced by enzymatic hydrolysis was assayed by gas chromatography on a .6'×2 mm (id) column packed with OV-101 (methylsilicone) on gas chrom Q (100-120 mesh), programmed from 125° to 175° C. Decyl pyroglutamate generated decanol with a t ½ of 1.7 min. by enzymatic hydrolysis.

EXAMPLE 3

Skin Irritation Study of Pyroglumate Esters

Fuzzy rats (Temple University) 150 to 200 g were used to study the dermal irritancy as the neat compounds. Test preparations (50 mg) were applied to circular gauze pads 1 mm thick and 16 mm in diameter, and affixed to the animals' dorsal surface with occlusive adhesive film (Adhesive Plaster for Patch Test, Kanebo, Ltd., Osaka, Japan). The occlusive dressings were removed after 3 or 7 days. Treated skin areas were then evaluated according to a modified Draize scoring method, and the irritation index was evaluated for each test site. The first or "primary irritation index" (PII) was an average value reflecting irritation both immediately after dressing removal, and 72 hours later. The "secondary irritation index" (SII) was determined 7 days after dressing removal. The maximum possible PII or SII was 8 with a total possible score of 4 erythema, and a total possible score of 4 for edema. A PII or SII less than or equal to 2 indicated a mild irritant, a PII or SII greater than 2 but less than or equal to 6 indicated a moderate irritant, and a PII greater than 6 indicated a severe irritant as shown in Table 1 below:

TABLE 1

Irritation data for pyroglutamate esters

| Sample (50 mg applied over 2 cm² surface) | Primary Irritation Index $T_0$–$T_{72}$hrs* 3 DAY occlusion | Secondary Irritation Index at 7 days 3 DAY occlusion |
|---|---|---|
| Decyl pyroglutamate | 0.9 ± 1.1 (4)** | 0 |
| Oleyl pyroglutamate | 0.1 ± 0.3 (4) | 0 |
| Dodecyl pyroglutamate | 0 (2) | 0 |
| Farnesyl pyroglutamate | 0 (2) | 0 |
| Azone | 4.0 ± 1.9 (5) | 0 |

*$T_0$ is time at which occlusive application is removed.
**Irritation index ± SD (n).

EXAMPLE 4

Permeation enhancement using pyroglutamate esters

In the examples given below, the permeation enhancement was determined using an in vitro diffusion cell procedure. The molts of adult *Elaphae obsolete* (black rat snake) was used as the model for stratum corneum membrane (R. Ibuki, Ph.D. Thesis, University of Kansas, 1985). The shed snake skin has great similarities to human skin in terms of thickness, composition of constituents and structure and has been proposed as the most suitable model for human stratum corneum for permeability studies.

Glass diffusion cells consisting of a donor and receptor cells separated by the shed snake skin membrane were assembled using circular O-ring joints held together by spring clamps. The exposed membrane surface area of the diffusion cell measured 1.8 cm². Before being mounted in the diffusion cell approximately 25 mg of an ointment containing the therapeutic agent and the penetration enhancer was carefully applied to the membrane and was spread over the desired area. The receptor side was filled with approximately 8.5 ml of buffer solution consisting of $1.5 \times 10^{-1}$ M NaCl, $5 \times 10^{-4}$ NaH$_2$PO$_4$ and $2.0 \times 10^{-4}$ M Na$_2$HPO$_4$ adjusted to pH 7.2 with NaOH. The diffusion cell was immersed vertically in a water bath maintained at 32°±1° C. The receptor cell was stirred constantly with a magnetic stirrer. To determine the amount of compound penetrated through the snake skin membrane from the upper chamber, 0.2 ml samples were withdrawn at varying intervals from the receptor chamber using a syringe. An equal amount of fresh buffer was replenished during sampling. The concentration of drug penetrated in each diffusion cell was measured using high pressure liquid chromatography. The results reported for each experiment are the average values from 5 replicate diffusion cells.

The ointments used for the experiments contained varying concentrations of the drug and penetration enhancing agent. The drug was dispersed in the enhancer and this was then mixed with white petrolatum USP using a vortex mixer around 55° C. The ointments were kept in a water bath at 32°±1° C. for 1 day before use in in vitro studies. See Tables II and III below for the results of penetration enhancement effects.

TABLE II

Penetration Enhancement of Indomethacin

| skin penetration enhancer | weight ratio of enhancer/indomethacin | flux of indomethacin µg/cm²/hr |
|---|---|---|
| n-Decyl pyroglutamate | 15.0 | 0.477 |
| n-Dodecyl pyroglutamate | 15.0 | 0.630 |
| Farnesyl pyroglutamate | 15.0 | 0.317 |
| Oleyl pyroglutamate | 15.0 | 0.450 |
| None | — | non-detectable |

TABLE III

Penetration Enhancement Using Dodecyl pyroglutamate

| Drug | weight ratio of enhancer/drug | flux of drug µg/cm²/hr |
|---|---|---|
| Hydrocortisone | 0 | Not detectable |
| " | 15 | 0.338 |
| Propranolol | 0 | 3.680 |
| " | 15 | 7.410 |

EXAMPLE 5

Percutaneous Delivery of 2,3-dihydro-5-hydroxy-6-(o-hydroxymethylcinnamyl)-benzofuran The transport of 2,3-dihydro-5-hydroxy-6-(o-hydroxymethylcinnamyl)benzofuran, through shed snake skin, which has been reported to be a good model for human stratum corneaum in terms of thickness, compositional features, structure and permeability, was measured in the presence of decyl, dodecyl and oleyl esters of L-pyroglutamic acid used as penetration enhancers.

Because of the poor aqueous solubility of 2,3-dihydro 5-hydroxy-6-(o-hydroxymethylcinnamyl)benzofuran (<0.0002 mg/ml at 32°), 20% propyleneglycol in isotonic pH 7.2 phosphate buffer was used as the receptor medium. Control experiments showed that the presence of 20% propylene glycol did not affect the barrier properties of snake skin. A weighed amount of a petrolatum ointment (30–35 mg) containing 1% (w/w) of 2,3-dihydro-5-hydroxy-6-(o-hydroxymethylcinnamyl)benzofuran with or without 15% (w/w) of the permeation enhancer was applied to 1.76 cm² area of shed skin of adult *Elaphae obsolata* (black rat snake), and held between the donor and receptor compartments of a diffusion cell by O-rings. The receptor compartment had a capacity of 8–9 ml. The diffusion cells were maintained at 32°±1° C. The amount of drug diffused into the receptor chamber was measured by HPLC using acetonitrile-water (2:3) at a flow rate of 1 ml/min as mobile phase, a $C_{18}$ column and a UV detector set at 260 mm. The results (Table IV below) are averages of five diffusion cells for each experiment.

The L-pyroglutamate esters were designed to act as "soft permeation enhancers," which after exercising their action at the stratum corneum barrier where the effect is desired, would undergo enzymatic breakdown into non-toxic metabolites in the viable tissue. Decyl L-pyroglutamate, for example, breaks down in rat plasma with t ½ of 1.7 minutes. These esters produced zero irritation in a modified Draize test involving three-day occlusive dermal application on fuzzy rats.

TABLE IV

Effects of Permeation Enhancers on the Delivery of 2,3-dihydro-5-hydroxy-6-(O-hydroxymethylcinnamyl)-benzofuran Through Snake Skin

| Permeation Enhancer | Flux µg/cm$^2$/hr ± SD | % delivered in 48 hrs ± SD |
|---|---|---|
| None | 0.19 | 4.24 ± 0.53 |
| Decyl L-pyroglutamate | 0.70 ± 0.06 | 16.1 ± 3.0 |
| Dodecyl L-pyroglutamate | 0.61 ± 0.04 | 13.4 ± 1.5 |
| Oleyl L-pyroglutamate | 0.95 ± 0.09 | 21.7 ± 1.1 |

*n = 5

Tables V–VI below, show permeation enhancement of enalapril, clonidine and acyclovir using various pyroglutamic esters.

TABLE V

Permeation Enhancement of Enalapril Using Pyroglutamate Esters

| Enhancer | Flux (µg/cm$^2$/hr) ± SD | % delivered in 48 hrs ± SD |
|---|---|---|
| None (n = 13) | — | 0.9 + 0.5 |
| Decyl pyroglutamate (n = 4) | 0.15 ± 0.01 | 4.3 + 0.9 |
| Dodecyl pyroglutamate (n = 4) | 0.51 ± 0.09 | 9.9 + 2.7 |
| Oleyl pyroglutamate (n = 5) | 0.92 ± 0.22 | 18.7 + 5.4 |

TABLE VI

Permeation Enhancement of Clonidine Using Pyroglutamate Esters

| Enhancer | Flux (µg/cm$^2$/hr) ± SD | % delivered in 48 hrs ± SD |
|---|---|---|
| None (n = 12) | — | 1.1 ± 0.3 |
| Decyl pyroglutamate (n = 4) | 0.31 ± 0.13 | 8.1 ± 2.1 |
| Dodecyl pyroglutamate (n = 4) | 0.63 ± 0.21 | 13.2 ± 0.6 |
| Oleyl pyroglutamate (n = 4) | 0.26 ± 0.15 | 4.4 ± 1.4 |

TABLE VII

Permeation Enhancement of Acyclovir Using Pyroglutamate Esters*

| Enhancer | Flux (µg/cm$^2$/hr) ± SD | % delivered in 48 hrs ± SD |
|---|---|---|
| None | — | not detectable |
| Decyl pyroglutamate | 0.063 ± 0.01 | 0.25 ± 0.03 |
| Dodecyl pyroglutamate | 0.072 ± 0.04 | 0.26 ± 0.15 |

*n = 4

What is claimed is:

1. A method of enhancing the rate of dermal absorption of a topically administered composition comprising a therapeutically effective dosage amount of a steroidal anti-inflammatory drug and a pyroglutamic acid ester absorption enhancing agent of the formula:

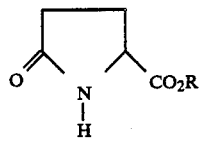

wherein R is a straight or branched chain alkyl ($C_5$–$C_{20}$), alkenyl ($C_5$–$C_{20}$) with 1–6 double bonds, hydroxyalkyl ($C_5$–$C_{20}$) with 1–3 hydroxy groups, ketoalkyl ($C_5$–$C_{20}$), unsaturated hydroxyalkyl ($C_5$–$C_{20}$), carboxyalkyl ($C_5$–$C_{20}$) or alkoxycarbonylalkyl ($C_5$–$C_{20}$).

2. The method of claim 1, wherein said drug is selected from the group consisting of hydrocortisone, hydrocortisone 17-valerate, hydrocortisone 17-butyrate, hydrocortisone 21-acetate, betamethasone valerate, triamcinolone acetonide, fluocinonide, desonide, fluocinolone acetonide, dexamethasone, prednisolone, haloprednone, cortisone acetate, cortisone cyclopentylpropionate, cortodoxone, flucetonide, fludrocortisone acetate, flurandrenolone acetonide, medrysone, amcinafal, amcinafide, betamethasone, betamethasone benzoate, chloroprednisone acetate, clocortolone acetate, descinolone acetonide, desoximetasone, dichlorisone acetate, diflupredvate, flucloronide, flumethasone, flunisolide acetate, fluocortolone, fluorometholone, fluperolone acetate, fluprednisolone, fluprednisolone valerate, meprednisone, methyl prednisolone, paramethasone acetate, prednisolamate, prednisone, predinival, triamcinolone, triamcinolone hexacetonide, cortivazol, formocortal and nivazol and said enhancing agent is represented when R is selected from the group consisting of alkyl, alkenyl hydroxyalkyl, ketoalkyl and alkoxycarbonylalkyl.

3. The method of claim 2, wherein said drug is hydrocortisone, prednisolone, methyl prednisolone, betamethasone, betamethasone benzoate or triamcinolone acetonide and said enhancing agent is represented when R is alkyl, alkenyl, hydroxyalkyl, ketoalkyl or alkoxycarbonylalkyl.

4. The method of claim 3, wherein said enhancing agent is represented when R is alkyl or alkenyl.

5. The method of claim 4, wherein R is alkyl.

6. The method of claim 4, wherein R is alkenyl.

7. A pharmaceutical composition for enhancing dermal absorption of a topically administered steroidal anti-inflammatory drug comprising a therapeutically effective dosage amount of said drug and a pyroglutamic acid ester enhancing agent of the formula:

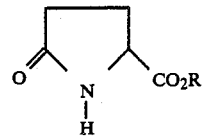

wherein R is a straight or branched chain alkyl ($C_5$–$C_{20}$), alkenyl ($C_5$–$C_{20}$) with 1–6 double bonds, hydroxyalkyl ($C_5$–$C_{20}$) with 1–3 hydroxy groups, ketoalkyl ($C_5$–$C_{20}$), unsaturated hydroxyalkyl ($C_5$–$C_{20}$), carboxyalkyl ($C_5$–$C_{20}$) or alkoxycarbonylalkyl ($C_5$–$C_{20}$).

8. The composition of claim 7, wherein said drug is selected from the group consisting of hydrocortisone, hydrocortisone 17-valerate, hydrocortisone 17-butyrate, hydrocortisone 21-acetate, betamethasone valerate, triamcinolone acetonide, fluocinonide, desonide, fluocinolone acetonide, dexamethasone, prednisolone, haloprednone, cortisone acetate, cortisone cyclopentylpropionate, cortodoxone, flucetonide, fludrocortisone acetate, flurandrenolone acetonide, medrysone, amcinafal, amcinafide, betamethasone, betamethasone benzoate, chloroprednisone acetate, clocortolone acetate, descinolone acetonide, desoximetasone, dichlorisone acetate, difluprednate, flucloronide, flumethasone, flunisolide acetate, fluocortolone, flurometholone, fluperolone acetate, fluprednisolone, fluprednisolone valerate, meprednisone, methyl prednisolone, paramethasone acetate, prednisolamate, prednisone, predival, triamcinolone, triamcinolone hexacetonide, cortivazol, formocortal and nivazol and said enhancing agent is represented when R is selected from the group consisting of alkyl, alkenyl, hydroxyalkyl, ketoalkyl and alkoxycarbonylalkyl.

9. The composition of claim 8, wherein said drug is hydrocortisone, prednisolone, methyl prednisolone, betamethasone, bridesonide, betamethasone benzoate or triamcinolone acetonide and said enhancing agent is represented when R is alkyl, alkenyl or hydroxyalkyl.

10. The composition of claim 9, wherein said drug is hydrocortisone, and said enhancing agent is represented when R is alkyl or alkenyl.

11. The composition of claim 10, wherein R is alkyl.

12. The composition of claim 11, wherein said alkyl is selected from the group consisting of octyl, decyl, dodecyl, tetradecyl, hexadecyl or eicosyl.

13. The composition of claim 12, wherein said alkyl is octyl.

14. The composition of claim 12, wherein said alkyl is decyl.

15. The composition of claim 12, wherein said alkyl is dodecyl.

16. The composition of claim 10, where R is alkenyl.

17. The composition of claim 16, wherein said alkenyl is selected from the group consisting of decenyl, dodecenyl, farnesyl, hexodecenyl, oleyl and octadecadienyl.

18. The composition of claim 17, wherein said alkenyl is farnesyl.

19. The composition of claim 17, wherein said alkenyl is oleyl.

20. The composition of claim 7 further comprising pharmaceutically acceptable excipients.

* * * * *